(12) United States Patent
Kim et al.

(10) Patent No.: US 11,427,537 B2
(45) Date of Patent: Aug. 30, 2022

(54) METHOD FOR PREPARING NATURAL L-CYSTEINE HYDROCHLORIDE HYDRATE CRYSTALS BY CONTINUOUS CHROMATOGRAPHY

(71) Applicant: CJ CheilJedang Corporation, Seoul (KR)

(72) Inventors: Jun-Woo Kim, Seoul (KR); Jung Min Lee, Seoul (KR); Se-Hee Jo, Seoul (KR); Il Chul Kim, Seoul (KR); In Sung Lee, Seoul (KR); Jun Young Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/962,622

(22) PCT Filed: Jan. 30, 2019

(86) PCT No.: PCT/KR2019/001286
§ 371 (c)(1),
(2) Date: Jul. 16, 2020

(87) PCT Pub. No.: WO2019/151769
PCT Pub. Date: Aug. 8, 2019

(65) Prior Publication Data
US 2020/0407313 A1 Dec. 31, 2020

(30) Foreign Application Priority Data
Jan. 31, 2018 (KR) .................... 10-2018-0012290

(51) Int. Cl.
*C07C 319/28* (2006.01)
*C07C 323/58* (2006.01)

(52) U.S. Cl.
CPC .......... *C07C 319/28* (2013.01); *C07C 323/58* (2013.01)

(58) Field of Classification Search
CPC ....... C07C 319/28; C07C 323/58; C12P 13/12
See application file for complete search history.

(56) References Cited

U.S. PATENT DOCUMENTS

| | | | |
|---|---|---|---|
| 6,946,268 B2 | 9/2005 | Takagi et al. | |
| 8,088,949 B2 | 1/2012 | Boehm | |
| 8,802,399 B2 | 8/2014 | Reutter-Maier et al. | |
| 9,120,729 B2 | 9/2015 | Leute et al. | |
| 2005/0221453 A1 | 10/2005 | Takagi et al. | |
| 2008/0190854 A1 | 8/2008 | Boehm | |

FOREIGN PATENT DOCUMENTS

| | | |
|---|---|---|
| EP | 1106602 A1 | 6/2001 |
| EP | 1234874 A1 | 8/2002 |
| EP | 1298200 A2 | 4/2003 |
| EP | 1571223 A2 | 9/2005 |
| EP | 1645623 A1 | 4/2006 |
| EP | 1650296 A1 | 4/2006 |
| JP | 2005-298369 A | 10/2005 |
| JP | 2008-194043 A | 8/2008 |
| KR | 10-1988-0000389 A | 3/1988 |
| KR | 10-2008-0011288 A | 2/2008 |
| KR | 10-2012-0041115 A | 4/2012 |
| KR | 10-2013-0136547 A | 12/2013 |
| WO | 2012/053794 A2 | 4/2012 |
| WO | 2013/089478 A2 | 6/2013 |

OTHER PUBLICATIONS

International Search Report issued in corresponding International Patent Application No. PCT/KR2019/001286 dated May 9, 2019.
Extended European Search Report issued in corresponding European Patent Application No. 19747674.0 dated Jan. 12, 2021.
Wu et al., "Design of Simulated Moving Bed Chromatography for Amino Acid Separations," Industrial & Engineering Chemistry Research, 37: 4023-4035 (1998).

*Primary Examiner* — Rosalynd A Keys
(74) *Attorney, Agent, or Firm* — Morgan, Lewis & Bockius LLP (57) ABSTRACT

The present disclosure relates to a method for preparing L-cysteine hydrochloride hydrate crystals, and L-cysteine hydrochloride hydrate crystals prepared by the method. Through the method for preparing L-cysteine hydrochloride hydrate crystals of the present disclosure, L-cysteine hydrochloride hydrate crystals can be obtained from a natural L-cysteine fermentation broth with a high recovery rate and/or purity without a chemical reaction or the use of an artificial synthetic compound.

14 Claims, 2 Drawing Sheets

METHOD FOR PREPARING NATURAL L-CYSTEINE HYDROCHLORIDE HYDRATE CRYSTALS BY CONTINUOUS CHROMATOGRAPHY

TECHNICAL FIELD

The present disclosure relates to a method for preparing L-cysteine hydrochloride hydrate crystals and L-cysteine hydrochloride hydrate crystals prepared by the method.

BACKGROUND ART

L-Cysteine is generally produced by decomposing animal-derived L-cysteine, which uses duck feathers or human hair as a source material, or fermentation-derived L-cysteine, which uses a microbial metabolism liquid as a source material, into L-cysteine by an electrochemical reduction reaction. In contrast, as methods for producing L-cysteine using microorganisms, there have been disclosed a process for producing natural L-cysteine by fermentation using a strain having a modified O-acetyl transferase in a medium containing sulfide (U.S. Pat. Nos. 8,802,399B, 6,946,268B), and a process for producing natural L-cysteine by mixing O-phosphohomoserine produced by a microbial culture method with sulfide and inducing an enzyme catalytic reaction using O-phosphoserine sulfhydrylase (WO2013/089478, WO2012/053794).

Although it has been disclosed that L-cysteine produced by the microbial culture method can be separated by ion exchange and other known methods, no information is given on the specific procedure, yield, purity, etc. (EP1645623A1, EP1298200B1, US20050221453A1, EP1234874A1, EP1571223A2, and EP1650296A).

Meanwhile, a method for producing L-cysteine hydrochloride monohydrate from an L-cysteine fermentation broth using ion exchange is known. For example, there has been disclosed a process for purifying L-cysteine with a yield of 90% or more by lowering the pH of a fermentation broth containing L-cysteine to a pH of 5 or below and then bringing it into contact with an acidic or strongly acidic cation exchanger such that L-cysteine binds to the ion exchanger, and eluting the bound L-cysteine with an aqueous hydrochloric acid solution. Accordingly, L-cysteine hydrochloride monohydrate can be produced using the L-cysteine hydrochloride eluent (U.S. Pat. No. 8,088,949B).

In addition, there has been disclosed a process for purifying L-cysteine with a yield of 85% or more, by bringing an L-cysteine-containing fermentation broth having a pH of 6 to 9 into contact with a basic anion exchanger, such that L-cysteine binds to the anion exchanger, eluting the bound L-cysteine with an aqueous hydrochloric acid solution, then bringing the eluate into contact with an acidic cation exchanger at a pH of 4 or below, such that the L-cysteine binds to the cation exchanger, and eluting the bound L-cysteine with an aqueous hydrochloric acid solution. Also, L-cysteine hydrochloride monohydrate can be produced using the L-cysteine hydrochloride eluent (U.S. Pat. No. 9,120,729B).

However, the above-described processes have disadvantages in that they involve a chemical reaction as they are carried out through repeated ion exchange steps, that they require a large amount of process water since a large amount of eluent is repeatedly used as a subsequent step of the ion adsorption process, and that an additional purification step must be carried out. Thus, there is a continuing need for a method for isolating L-cysteine with a higher yield and purity and producing L-cysteine hydrochloride hydrate.

Under these circumstances, the present inventors have made extensive efforts to increase the purity and yield of L-cysteine hydrochloride hydrate, and have completed a method for producing L-cysteine hydrochloride hydrate including the advantages of having increased effective productivity and reduced water consumption as well as high yield and purity.

DISCLOSURE

Technical Problem

One object of the present disclosure is to provide a method for preparing L-cysteine hydrochloride hydrate crystals.

Another object of the present disclosure is to provide L-cysteine hydrochloride hydrate crystals prepared by the method for preparing L-cysteine hydrochloride hydrate crystals.

Technical Solution

Hereinbelow, the present disclosure will be described in detail.

Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In addition, those skilled in the art can recognize and identify numerous equivalents for the specific embodiments of the invention disclosed herein using no more than routine experimentation, and all such equivalents are believed to be within the scope of the invention.

In one aspect of the present disclosure to overcome the objects above, there is provided a method for preparing L-cysteine hydrochloride hydrate crystals, comprising:

(a) obtaining a separated liquid after introducing a fermentation broth in a pH range of 3.0 to 9.0 containing L-cysteine into a continuous chromatography apparatus having a strongly acidic cation-exchange resin as a stationary phase;

(b) adding hydrochloric acid to the separated liquid such that the equivalence ratio ([HCl]/[L-cysteine]) of hydrochloric acid to L-cysteine is from 0.9 to 3.0;

(c) concentrating the separated liquid to which hydrochloric acid is added; and (d) recovering L-cysteine hydrochloride hydrate crystals from the concentrate liquid.

As used herein, the term "L-cysteine" is one of the constituent amino acids and is the only sulfur-containing amino acid having a thiol group (R—SH) among L-amino acids. L-Cysteine may be obtained by chemical synthesis, or biological synthesis through microbial fermentation, etc., but is not limited thereto. Specifically, in the present disclosure, L-cysteine may be L-cysteine biologically produced through microbial fermentation, or may be natural L-cysteine obtained by inducing an enzyme catalytic reaction of O-phosphohomoserine, which is a precursor prepared through microbial fermentation, with a sulfide in the presence of phosphoserine sulfhydrylase. In terms of the preparation process, the natural L-cysteine may be L-cysteine obtained without going through a chemical reaction, chemical adsorption, or elution.

As used herein, the term "natural" indicates that something does not depend on a chemical reaction. According to the EU Flavorings Regulation 1334/2008, only substances obtained by a physical, enzymatic, or microbial process are defined as "natural" flavoring agents. From the above viewpoint, regardless of whether it is derived from an animal or microbial fermentation, L-cysteine produced by an electrochemical reduction reaction of L-cysteine cannot be called entirely natural.

As used herein, the term "fermentation broth" refers to a culture medium obtained by culturing L-cysteine-producing microorganisms, a culture containing the microorganisms cultured together with the culture medium, or an enzyme conversion solution containing a precursor capable of producing L-cysteine and an enzyme. Specifically, the fermentation broth containing L-cysteine may be a culture medium or an enzyme conversion solution containing natural L-cysteine. More specifically, it may be an L-cysteine culture or culture medium biologically prepared by fermenting microorganisms having an L-cysteine-producing ability, or a natural L-cysteine enzyme conversion solution obtained by inducing an enzyme catalytic reaction of O-phosphohomoserine, which is a precursor prepared through microbial fermentation, with a sulfide in the presence of phosphoserine sulfhydrylase. L-Cysteine hydrochloride hydrate crystals prepared by using the fermentation broth as a source liquid do not depend on a chemical reaction and thus can be implied as being derived from nature.

In the present disclosure, the fermentation broth can be used as a source liquid for a continuous chromatography process. That is, it may be introduced into the continuous chromatography apparatus of step (a).

The pH of the fermentation broth to be introduced into the continuous chromatography apparatus may vary depending on the preparation method, but may be in the range of 2.5 to 9.5, 2.5 to 9.0, 3.0 to 9.0, 3.5 to 8.5, 3.5 to 7.5, 4.5 to 7.0, or 5.0 to 6.0. The fermentation broth itself may be used as a source liquid for the continuous chromatography, and a step of adjusting the fermentation broth containing L-cysteine to a pH of 2.5 to 9.5, 2.5 to 9.0, or 3.0 to 9.0, specifically 3.5 to 8.5, or 3.5 to 7.5, more specifically 4.5 to 7.0, or 5.0 to 6.0 may further be included. For example, the pH may be adjusted by adding an acid such as sulfuric acid or hydrochloric acid, or a base such as sodium hydroxide (caustic soda), ammonia, lithium hydroxide, or potassium hydroxide, etc., but is not limited thereto. The pH-adjusting agent can be appropriately selected and used by those skilled in the art so long as crystals of L-cysteine hydrochloride hydrate can be obtained without affecting the structure of L-cysteine.

As the pH of the fermentation broth of L-cysteine is lowered, there is a strong tendency for L-cysteine to cationize. As the stationary phase of the continuous chromatography used herein is a strongly acidic cation-exchange resin, it tends to adsorb cations, so that when L-cysteine is cationized, it may be partially adsorbed onto the stationary phase, thereby reducing the recovery rate of the continuous chromatography process. In addition, L-cysteine has a strong tendency to be oxidized and converted to L-cysteine at higher pH, which may reduce the recovery rate of the continuous chromatography process. Thus, the fermentation broth containing L-cysteine may be a fermentation broth having a pH of 2.5 to 9.5, specifically 3.0 to 9.0, more specifically 3.5 to 8.5, even more specifically 3.5 to 7.5, 4.5 to 7.0, or 5.0 to 6.0.

However, as the recovery rate of the continuous chromatography process may be affected by various process parameters, such as the flow rate between resin towers of the continuous chromatography process, the temperature of the process, the composition of the mobile phase, the continuous chromatography sequence, etc., the recovery rate of the continuous chromatography process is not a factor that is limited only by the pH of the source liquid for the continuous chromatography.

In the present disclosure, the method may further include a step of diluting or concentrating the fermentation broth containing L-cysteine prior to step (a). The step may be carried out before or after the step of adjusting pH described above.

The concentration may be carried out in a conventional evaporator (for example, a forced circulation evaporator, a thin film evaporator, or a rotary evaporator, etc.).

The concentration of L-cysteine in the diluted or concentrated fermentation broth may be adjusted to 10 g/L to 180 g/L, specifically 10 g/L to 150 g/L, but it is not a factor that greatly affects the recovery rate of the continuous chromatography process and the quality of the separated liquid (specifically, the solid content of L-cysteine excluding moisture in the separated liquid) obtained through the continuous chromatography process. Thus, to adjust the concentration of the fermentation broth containing L-cysteine used as a source liquid for the continuous chromatography process is not an essential process for separating and purifying L-cysteine. However, when the concentration is adjusted to 180 g/L or more, the concentration of L-cysteine is higher than the solubility of L-cysteine, so that low-quality L-cysteine crystals are produced which are inadequate for recovery, resulting in the deterioration of the recovery rate of the continuous chromatography process. When the concentration of the source liquid for the continuous chromatography process is high, the amount of water used in the continuous chromatography process may be reduced relative to the amount of L-cysteine used for treatment. Such a feature cannot be found in an ion-exchange process in which the amount of water used is determined by the maximum adsorption amount of L-cysteine and an ion-exchange resin.

As used herein, the term "continuous chromatography" refers to a process by which a conventional batch chromatography process is carried out continuously. Specifically, a solid phase and a liquid phase can be continuously supplied to the chromatography apparatus, and the solid phase and the liquid phase move in opposite directions to each other to cause the countercurrent contact, thereby enabling the separation of substances more efficiently. In the present disclosure, the continuous chromatography may be used in the sense that it includes both true moving bed (TMB) chromatography and simulated moving bed chromatography (SMB). In addition, since the true moving bed chromatography and the simulated moving bed chromatography employ the same principles, they can be appropriately selected and used by those skilled in the art in consideration of the productivity and other matters.

When the continuous chromatography process is employed in the present disclosure, an adsorption/elution process is not required, and thus, it has the advantages of having a high productivity per hour compared to an ion-exchange process and reducing the amount of water used in the process. In addition, in order to obtain an L-cysteine powder product from a process liquid containing L-cysteine obtained by an ion-exchange process or common chromatography process in a high yield, a large amount of energy is required in a concentration crystallization process. In this regard, the energy cost may be reduced according to the method of the present disclosure.

Figure 1:
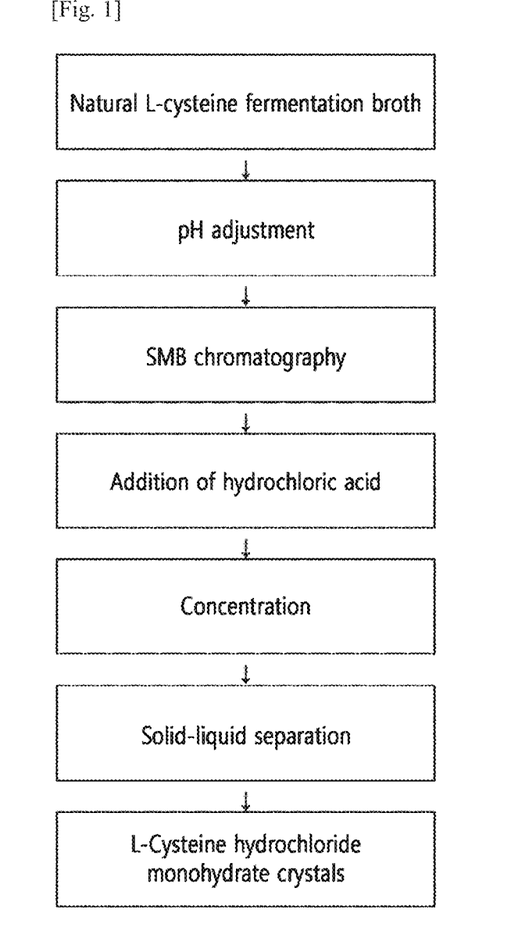
FIG. 1 shows a representative illustration of a process for preparing L-cysteine hydrochloride hydrate crystals by continuous chromatography from natural L-cysteine contained in a fermentation broth.
Figure 2:
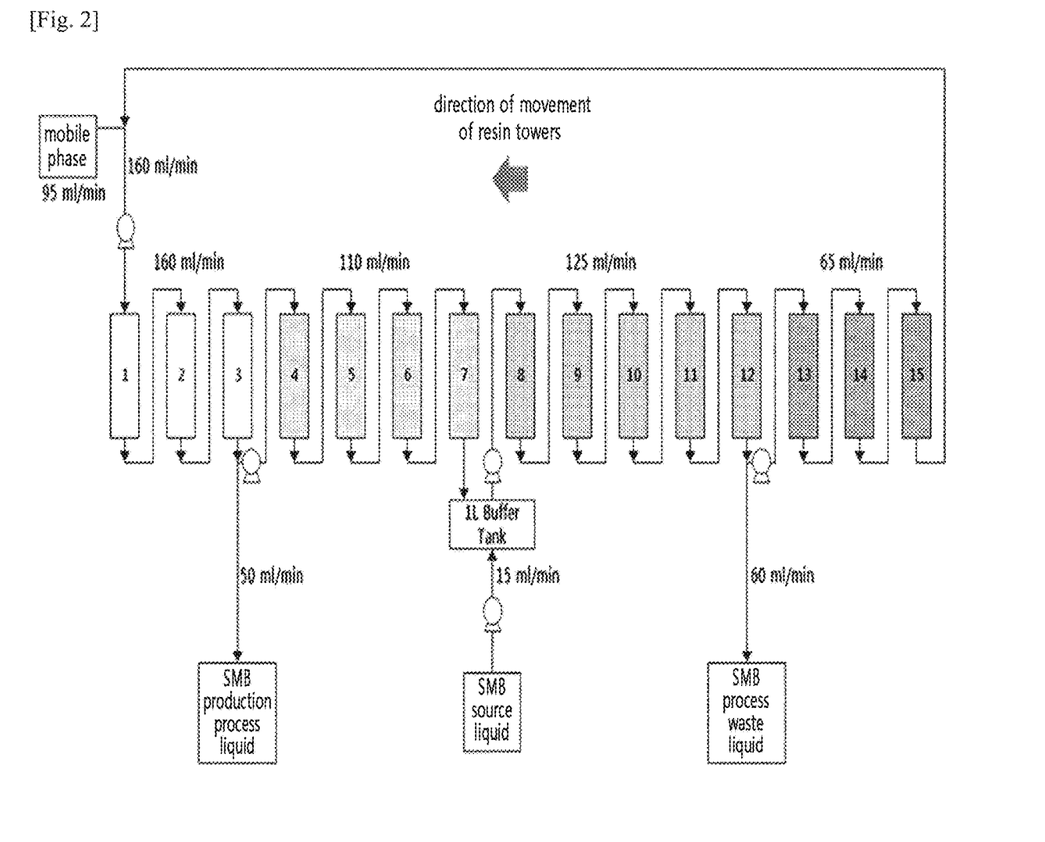
FIG. 2 shows the arrangement of resin towers and the flow rate for each section of SMB chromatography used in one embodiment of the present disclosure.

In an embodiment of the present disclosure, an SMB chromatography apparatus may be used, and a schematic diagram of the SMB chromatography apparatus is shown in FIG. 2. The process parameters such as the number of resin towers, the volume of the resin towers, the filling capacity of resin, the flow rate of each section, the presence or absence of buffer tank installation, the movement time of the resin towers, etc. may vary, and are not limited to the fixed conditions specified above.

The stationary phase of the continuous chromatography apparatus may be an ion-exchange resin, and specifically, it may be a strongly acidic cation-exchange resin. The functional group of the strongly acidic cation-exchange resin may be a sulfonic group, but is not limited thereto. In addition, the parent compound of the strongly acidic cation-exchange resin used herein is not limited as long as a strongly acidic functional group can be attached thereto. For example, those derived from a styrene-divinylbenzene copolymer may be used, but are not limited thereto. In a specific example, the strongly acidic cation-exchange resin may be a styrene-divinylbenzene sulfonic acid copolymer, but is not limited thereto.

When styrene-divinylbenzene copolymers having no functional group, exchange resins having no functional group such as methacrylate polymers having no functional group; strongly basic anion-exchange resins such as trimethylamine styrene-divinylbenzene copolymers; weakly basic anion-exchange resins such as tertiary amine styrene-divinylbenzene copolymers; weakly basic cation-exchange resins such as carboxyl methacrylate polymers, etc., are used in the present disclosure as other types of stationary phases commonly used in the separation and purification of amino acids in the art, it is difficult to purify L-cysteine in a solid content of 50% (w/w) or more excluding moisture in the separated liquid obtained through the continuous chromatography process. Meanwhile, when a strongly acidic cation-exchange resin such as a styrene-divinylbenzene sulfonic acid copolymer is used, it is possible to purify L-cysteine in a solid content of 80% (w/w) or more excluding moisture in the separated liquid obtained through the continuous chromatography process, specifically 90% (w/w) or more.

In the chromatography apparatus, water to which no chemical compounds (such as an organic solvent such as methanol, isopropyl alcohol, acetonitrile, etc.) are added, a caustic soda diluted solution, a sulfuric acid diluted solution, a phosphoric acid diluted solution, a hydrochloric acid diluted solution, a potassium hydroxide diluted solution, or a mixture thereof may be used as a mobile phase, but is not limited thereto. In a specific example, water may be used as a mobile phase for the continuous chromatography. When a mobile phase containing a chemical compound is used, the chemical compound may remain in the final product, so that it may not be possible to sell the product as it may have exceeded the standard residue limit for the chemical compound, or it may be impossible to distribute the product as a natural product. In addition, since no chemical substances other than water are added to the process water, a production cost-saving effect can be expected. In the ion-exchange process, in order to elute the bound L-cysteine, a solvent such as hydrochloric acid or sulfuric acid is essentially used as an eluent, and accordingly, its use is inevitably accompanied by an increase in the product cost associated with the use and disposal of the chemical substances.

When the fermentation broth containing L-cysteine is introduced into the continuous chromatography apparatus in step (a), a separated liquid containing L-cysteine can be obtained as L-cysteine is separated according to the continuous chromatography. In the present disclosure, the separated liquid containing the separated L-cysteine may be briefly referred as a "separated liquid", a "chromatography separated liquid", or a "process liquid".

The quality of the separated liquid may be evaluated by the content of L-cysteine in the solid excluding moisture in the separated liquid. The separated liquid of the present disclosure may have a solid content of L-cysteine excluding moisture of 80% (w/w), specifically 85% (w/w), more specifically 90% (w/w) or more. It was experimentally confirmed that L-cysteine hydrochloride hydrate crystals having a purity of 98% or more can be prepared when the solid content of L-cysteine excluding moisture in the separated liquid is 80% or more. However, since the purity of the L-cysteine hydrochloride hydrate crystals may be affected by other process conditions such as concentration, crystallization, crystal separation, etc., the purity of the L-cysteine hydrochloride hydrate crystals is not a factor that is limited only by the solid content of L-cysteine excluding moisture in the process liquid produced by the continuous chromatography.

In the present disclosure, step (a) may be referred to as a "continuous chromatography process". The term "the recovery rate of the continuous chromatography process" refers to the recovery rate of L-cysteine in the separated liquid obtained relative to the fermentation broth introduced in step (a), and is used to evaluate the efficiency of the process. The recovery rate of the continuous chromatography in the present disclosure may be 50% (w/w), specifically 60% (w/w), more specifically 70% (w/w), and more specifically 80% (w/w) or more, but is not limited thereto.

In order to convert L-cysteine contained in the separated liquid of the present disclosure into L-cysteine hydrochloride, hydrochloric acid may be added to the separated liquid in step (b). Specifically, hydrochloric acid may be added such that the equivalence ratio ([HCl]/[L-cysteine]) of hydrochloric acid to L-cysteine contained in the separated liquid is greater than 0.85 and 3.5 or less, greater than 1.0 and less than 3.0, 0.9 to 3.0, specifically, 1.5 to 2.5, more specifically, 2.0. When the equivalence ratio is 0.9 to 3.0, the recovery rate of the crystallization process may be 40% or more, and it is expected to be 50% or more at the equivalence ratio of greater than 1.0 and less than 3.0, and the recovery rate of the crystallization process may be 60% or more at the equivalence ratio of 1.5 to 2.5.

Step (c) is a step for concentrating the separated liquid to which hydrochloric acid is added for crystallization. In step (c), a concentrate may be obtained by concentrating the separated liquid to which hydrochloric acid is added. The concentration may be carried out in a conventional evaporator (for example, a forced circulation evaporator, a thin film evaporator, or a rotary evaporator, etc.) by those skilled in the art via an appropriate selection. The concentration of L-cysteine in the concentrate of step (c) may be in the range of 100 g/L to 900 g/L, specifically 200 g/L to less than 900 g/L, 300 g/L to less than 900 g/L, 400 g/L to less than 900 g/L, more specifically less than 500 g/L to 900 g/L.

When the concentration of L-cysteine in the concentrate is low, crystallization does not occur during concentration due to lack of supersaturation required for nucleation and crystal growth, and crystallization may be achieved during cooling, or crystallization may be carried out through an additional process. However, the recovery rate may be low, or the crystallization time may be prolonged. When the concentration of L-cysteine in the concentrate is 300 g/L or more, crystal nuclei of L-cysteine hydrochloride hydrate may be formed during the concentration process. Additionally, when the L-cysteine hydrochloride hydrate slurry concentrated to 300 g/L or more is cooled, the recovery rate of the crystallization process for the L-cysteine hydrochloride hydrate may increase. When the concentration of the L-cysteine hydrochloride hydrate in the concentrate is 900 g/L, solidification may occur due to the formation of a large amount of crystal particles, and accordingly, stirring of the crystal slurry and crystal separation may not be possible. Therefore, the step of concentrating the separated liquid to which hydrochloride acid is added is concentrated so that the concentration of L-cysteine is 200 g/L to less than 900 g/L, specifically 300 g/L to less than 900 g/L, more specifically 500 g/L to less than 900 g/L.

The crystallization of L-cysteine hydrochloride hydrate may occur during the concentration according to step (c). As used herein, the term "crystallization" refers to a phenomenon by which a liquid or a solid in amorphous state forms a crystal, and is accompanied by two phenomena called nucleation and crystal growth.

The concentrate may form and/or grow crystal nuclei through cooling and/or aging prior to recovery. Further, even when the L-cysteine hydrochloride hydrate crystals are not precipitated from the concentrate, crystals may be formed during cooling or aging of the concentrate.

The cooling step may specifically refer to cooling to a temperature of −10° C. to 55° C. over a period of 2 hours to 6 hours, specifically cooling to a temperature of 0° C. to 45° C. over a period of 2 hours to 6 hours, more specifically cooling to a temperature of 0° C. to 30° C., and even more specifically cooling to a temperature of 0° C. to 15° C. over a period of 2 hours to 6 hours. The aging step may refer to allowing to stand without changing the temperature. In the present disclosure, it may refer to constantly maintaining the cooled temperature, or it may refer to constantly maintaining the temperature of the concentrate even when it is not cooled. Specifically, the aging may be achieved over a period of 1 hour to 3 hours.

The series of step (c) in the present disclosure may be referred to as a "crystallization process". The "recovery rate of the crystallization process" refers to the L-cysteine recovery rate of the L-cysteine hydrochloride hydrate crystals obtained relative to the L-cysteine in the separated liquid according to the continuous chromatography process, and is used to evaluate the efficiency of the crystallization process. The recovery rate of the continuous chromatography process recovery may be 40% (w/w), specifically 50% (w/w), more specifically 60% (w/w), even more specifically 70% (w/w).

In step (d), the L-cysteine hydrochloride hydrate crystals precipitated from the concentrate may be recovered. Specifically, the L-cysteine hydrochloride hydrate crystals may be recovered from the slurry by subjecting the concentrate to a solid-liquid separation. This may be carried out using a solid-liquid separator such as a reduced-pressure membrane filtration apparatus, a pressure membrane filtration apparatus, a centrifugal separation apparatus, etc., but is not limited thereto. The slurry and/or precipitated cysteine crystals may be subjected to additional washing or drying.

In the present disclosure, the filtrate obtained by recovering the crystals in step (d) is a mother liquid having residual L-cysteine, and may be wholly or partially added to the fermentation broth of step (a), the separated liquid of step (b), or the separated liquid to which hydrochloric acid is added of step (c), in order to enhance the recovery rate during the final purification of L-cysteine, but is not limited thereto.

The L-cysteine hydrochloride hydrate prepared according to the preparation method of the present disclosure may be a monohydrate. The purity of the L-cysteine hydrochloride hydrate crystals prepared according to the preparation method of the present disclosure may be 95% (w/w) or more, specifically 98% (w/w), more specifically 99% (w/w).

In another aspect of the present disclosure to overcome the objects above, there is provided L-cysteine hydrochloride hydrate crystals prepared by the method for preparing L-cysteine hydrochloride hydrate crystals described above.

The crystals of L-cysteine hydrochloride hydrate and the preparation method thereof are as described above.

Advantageous Effects

The method for preparing L-cysteine hydrochloride hydrate crystals of the present disclosure is capable of separating and purifying the L-cysteine fermentation broth as it is in the natural state without a chemical reaction or the use of artificial synthetic compounds, and obtaining L-cysteine hydrochloride hydrate crystals with a high recovery rate and/or purity at the same time. In addition, the preparation method of the present disclosure shows efficient productivity, and in particular, water consumption can be remarkably reduced.

MODE FOR INVENTION

Hereinafter, the present disclosure will be described in more detail by way of Examples. However, these Examples are given for illustrative purposes only, and the scope of the invention is not intended to be limited by these Examples.

Test Methods

Common analytical methods used in Examples of the present disclosure are as follows:

(1) HPLC for Quantitative Analysis of L-Cysteine Hydrochloride Monohydrate

The conditions for HPLC analysis for analyzing the purity and concentration of L-cysteine hydrochloride monohydrate in the present disclosure are as follows:

Apparatus: HPLC 1260 Infinity System (Agilent Technology Inc.)

Column: HP C18 (150 mm×3.9 mm; 5 μm)

Mobile phase: Acetonitrile/Water/Heptafluorobutyric acid (8/92/0.1)

Flow rate: 0.425 mL/min

Temperature: 30° C.

Detection: UV at 220 nm

Volume of sample introduced: 2 μL (2) Method for Measuring Purity of L-Cysteine Hydrochloride Monohydrate Crystals In the present disclosure, the quality of L-cysteine hydrochloride monohydrate crystals is evaluated based on the purity of L-cysteine hydrochloride monohydrate, and the procedure thereof is as follows:

(a) Preparing L-cysteine hydrochloride anhydrous crystals by placing L-cysteine hydrochloride monohydrate crystals in a vacuum dryer containing silica gel for 24 hours under a vacuum of 20 mmHg or below to remove residual moisture and cooling the temperature of L-cysteine hydrochloride anhydrous crystals to room temperature;

(b) Preparing a sample of 0.5000 g/L by quantitatively measuring 0.5000 g of the L-cysteine hydrochloride anhydrous crystals cooled to room temperature, placing it in a 1 L volumetric flask, and diluting it with triple-distilled water;

(c) Preparing a sample of 0.5000 g/L by quantitatively measuring 0.5000 g of the L-cysteine hydrochloride anhydrous crystals, placing it in a 1 L volumetric flask, and diluting it with triple-distilled water, after treating L-cysteine hydrochloride monohydrate standard crystals (Sigma, ≥99.0%) in the same manner as in step (a), subsequently, determining the purity of a standard product through the certificate of the standard reagent manufacturer, and then converting the concentration of L-cysteine hydrochloride anhydrous in the sample (converted [concentration of L-cysteine hydrochloride anhydrous] is 0.5000 g/L×[purity of standard product]); and (d) Analyzing the purity of the L-cysteine hydrochloride anhydrous crystals used in step (a) by using the sample prepared in step (c) as an external standard and analyzing the sample prepared in step (b) by HPLC (the purity of the analyzed L-cysteine hydrochloride anhydrous crystals is the same as the purity of the L-cysteine hydrochloride monohydrate crystals).

(3) Method for Analyzing the Content of L-Cysteine Based on Solids in the Fermentation Broth or Separated Liquid According to Chromatography Process In the present disclosure, the quality of the fermentation broth or the separated liquid according to the chromatography process is evaluated based on the content of L-cysteine in the solids obtained by removing moisture from the solution, and the procedure thereof is as follows:

(a) Deodorizing a porcelain container with about 5 g of sea sand (10 to 20 mesh; Daejung Chemicals) and removing the residual moisture by placing it in a forced circulation oven at 105° C. for 3 hours, and then cooling it to room temperature by placing it in a vacuum dryer containing silica gel for 1 hour;

(b) Adding the solution to be analyzed to the container of step (a), and quantifying the [mass of solution] using the weight difference before and after the addition;

(c) Removing the residual moisture by placing the container in a forced circulation oven at 105° C. for 3 hours, and then cooling it to room temperature by placing it in a vacuum dryer containing silica gel for 1 hour, subsequently, quantifying the amount of moisture removed using the weight difference, and converting the solid content by mass of the solution to be measured using the same ([solid content by mass] is ([mass of solution]−[mass of removed moisture])/[mass of solution]);

(d) Measuring the density of the solution to be analyzed using a specific gravity analyzer;

(e) Measuring the concentration of L-cysteine in the solution to be analyzed by HPLC; and (f) Converting the content of L-cysteine in the solid excluding moisture in the solution to be analyzed using the solid content by mass of the solution, density, and the concentration of L-cysteine ([content of L-cysteine in the solid excluding moisture in the solution] is [concentration of L-cysteine]/[density of solution]/[solid content by mass of solution]).

PREPARATION EXAMPLE (1) Preparation of Fermentation Broth Containing L-Cysteine

After obtaining an O-phosphoserine fermentation broth by culturing a microorganism capable of producing O-phosphoserine in a fermentation medium, the fermentation broth was subjected to an enzyme conversion reaction with a sulfide using O-phosphoserine sulfhydrase (OPS sulfhydrase) to obtain a fermentation broth containing L-cysteine.

Specifically, KCCM 11103P (CA07-0022/pCL-prmf-serA*(G336V)-serC; Korean Patent No. 10-1381048) strain, which is a modified E. coli W3110 strain in which serB is deleted and mutant serA* is introduced to have an OPS-producing ability, was cultured on an MMYE agar plate at 33° C. for 24 hours and ⅒ of the cells on the plate were scraped from one plate and inoculated into a flask seed medium (10 g/L of glucose, 0.5 g/L of magnesium sulfate, 3 g/L of potassium dihydrogenphosphate, 10 g/L of yeast extract, 0.5 g/L sodium chloride, 1.5 g/L ammonium chloride, 12.8 g/L sodium pyrophosphate, 1 g/L glycine) in a baffle flask to carry out a seed culture at 200 rpm at 30° C. for 6 hours. After the seed culture was completed, the seed culture medium with a volume corresponding to 16% of the volume of the main culture medium was inoculated into a 1 L small-size fermenter filled with 300 mL of the main culture medium, and the culture was carried out at 33° C. at pH 7.0 to obtain an OPS fermentation broth. 50 mM OPS fermentation broth was reacted with Mycobacterium tuberculosis H37Rv-derived 50 mg/mL Msm-T enzyme under a condition of 100 mM $Na_2S$ and 0.2 mM pyridoxal 5'-phosphate (PLP) to obtain a fermentation broth containing L-cysteine (Korean Patent No. 10-1381048).

The pH of the L-cysteine fermentation broth was 9.3 and the concentration of L-cysteine was 26 g/L. The solid content of L-cysteine excluding moisture in the L-cysteine fermentation broth was 26.7%. The pH of the fermentation broth was adjusted by lowering to a pH of 5.5 using 98% sulfuric acid. The fermentation broth was concentrated using a thin film evaporator to prepare an L-cysteine fermentation broth having an L-cysteine concentration of 120 g/L as a source liquid for SMB chromatography. The concentration conditions are as follows:

Internal pressure: 80 mmHg
Steam pressure: 2 bar
Maximum injection amount: 100 L
Forced circulation flow rate of process liquid: 10 L/min
Evaporation rate: about 25 L/hr (2) Obtaining Separated Liquid in which L-Cysteine is Separated Using Continuous Chromatography Apparatus In order to obtain a separated liquid in which L-cysteine was separated, an SMB chromatography apparatus was used. A schematic diagram of the SMB chromatography apparatus is shown in FIG. 2.

Specifically, as shown in FIG. 2, the apparatus was composed of a total of 15 resin towers. The volume of each tower was 1.5 L, and the resin was filled to 95% of the tower volume. The SMB source liquid was introduced into resin tower 8 at a flow rate of 15 mL/min. The mobile phase was introduced into resin tower 1 at a flow rate of 95 mL/min. The SMB production process liquid (separated liquid) was discharged from resin tower 3 at a flow rate of 50 mL/min. The SMB process waste liquid was discharged from resin tower 12 at a flow rate of 60 mL/min. The liquid discharged from resin tower 15 was mixed with the mobile phase at a flow rate of 65 mL/min and then the mixture was introduced into resin tower 1 at a total flow rate of 160 mL/min. A 1 L buffer tank was installed between resin towers 7 and 8 to enable automatic control by controlling the water level so that the source liquid for SMB chromatography could flow into the resin towers at a constant flow rate. The resin towers were moved in the direction of decreasing number every 8 minutes, but they were driven in a circulating manner such that resin tower 1 was moved to resin tower 15.

In the Preparation Example, each of TRILITE® MCK32L, PUROLITE® PCR642, or DIAION® UBK555 resins, which are styrene-divinylbenzene copolymer resins having a strong acid sulfonic group as a functional group, was loaded into the resin tower of the chromatography apparatus, and 0.1 kL or more of the source liquid for SMB chromatography was introduced thereto. Then, the apparatus was operated to obtain an SMB production process liquid (separated liquid). The separated liquids had a pH of 6.1, 6.3, and 5.9, respectively, and the concentration of L-cysteine was 35.1 g/L, 34.8 g/L, and 33.9 g/L, respectively.

(3) Hydrochloric Acid Addition Reaction and Concentration

36% hydrochloric acid was added to the above separated liquid so that the [HCl]/[L-cysteine] equivalence ratio was 2, and the liquid was concentrated by linearly connecting a thin film concentration tube and a forced circulation-type concentration tube until the concentration of L-cysteine reached 700 g/L. The L-cysteine hydrochloride monohydrate crystals were precipitated during the concentration, and the temperature of the L-cysteine hydrochloride monohydrate crystal slurry was 55° C. immediately after the concentration. The concentration conditions are as follows:

Internal pressure: 80 mmHg
Steam pressure: 2 bar
Maximum injection amount: 100 L
Forced circulation flow rate of process liquid: 10 L/min
Evaporation rate: about 10 L/hr (4) Cooling and Recovery of L-Cysteine Hydrochloride Crystals The L-cysteine hydrochloride monohydrate crystal slurry was cooled in a jacket tank to 15° C. for 4 hours at a constant cooling rate while stirring, and stirred for 2 hours at the same temperature as the temperature at the completion of cooling. Thereafter, the L-cysteine hydrochloride monohydrate crystals were subjected to a solid-liquid separation from the L-cysteine hydrochloride monohydrate crystal slurry using a basket centrifugal separator. The separation conditions of the basket separator are as follows:

Equipment: 4.5 L basket separator (H-122; Kokusan)
Washing liquid: triple-distilled water
Filter type: Polyamide multifilament fiber filter fabric
Filter air permeability: 250 L/m²/s (at 2 mbar)
Bowl rotation speed: 3,000 rpm
Bowl rotation time: 20 min During the separation, the washing liquid was added 10% of the volume of the L-cysteine hydrochloride monohydrate crystal slurry. After the separation, the resultant was dried at 35° C. for 2 hours or more using a fluidized bed dryer to lower the residual moisture to 12.0% or below, and finally, L-cysteine hydrochloride monohydrate crystals were prepared.

Accordingly, the yield of the SMB chromatography process, the solid content of L-cysteine (%) in the separated liquid obtained through the SMB chromatography process, and the purity of the L-cysteine hydrochloride monohydrate crystals were measured. The recovery rate of the SMB chromatography process was calculated as the recovery rate of L-cysteine in the separated liquid compared to the fermentation broth introduced into the SMB chromatography apparatus. The results are shown in Table 1 together with the results obtained in the Preparation Example. When a styrene-divinylbenzene copolymer resin having a sulfonic group as a functional group was used as a stationary phase, all of the experimental results showed that the yield of the SMB chromatography process was more than 90%, that the solid content of L-cysteine excluding moisture in the separated liquid obtained through the SMB chromatography process was 92.5% or more, and that the purity of the L-cysteine hydrochloride monohydrate crystals was 99.5% or more.

Based on this, it can be confirmed that when the continuous chromatography is carried out by employing a stationary phase resin having a strongly acidic functional group, L-cysteine hydrochloride monohydrate crystals can be obtained with a higher yield and purity.

Experimental Example 1—Evaluation According to Types of Ion-Exchange Resins

In the preparation Example, L-cysteine hydrochloride hydrate crystals were prepared by only varying the stationary phase resins loaded into the SMB chromatography apparatus. As the resins used as the stationary phase, those which can be industrially used without difficulty and which can be produced by mass production were selected. The resins were selected based on the functional groups, such that they contain a weakly acidic carboxyl group, a strong basic trimethylamine group, a weak basic tertiary amine group, and no functional group.

Accordingly, the yield of the SMB chromatography process, the solid content of L-cysteine (%) in the separated liquid obtained through the SMB chromatography process, and the purity of the L-cysteine hydrochloride monohydrate crystals finally recovered were measured. The recovery rate of the SMB chromatography process was calculated as the recovery rate of L-cysteine in the separated liquid compared to the fermentation broth introduced into the SMB chromatography apparatus. The results are shown in Table 1 together with the results obtained in the Preparation Example.

TABLE 1

| Type of stationary phase | Component | Functional group | Yield of SMB chromatography (%) | Content of L-cysteine (%) | Purity of L-cysteine hydrochloride monohydrate crystals (%) |
|---|---|---|---|---|---|
| TRILITE ® MCK32L | Styrene-divinylbenzene copolymer | Sulfonic group | 92.4 | 93.2 | 99.7 |
| PUROLITE ® PCR642 | Styrene-divinylbenzene copolymer | Sulfonic group | 90.8 | 92.9 | 99.5 |

TABLE 1-continued

| Type of stationary phase | Component | Functional group | Yield of SMB chromatography (%) | Content of L-cysteine (%) | Purity of L-cysteine hydrochloride monohydrate crystals (%) |
|---|---|---|---|---|---|
| DIAION® UBK555 | Styrene-divinylbenzene copolymer | Sulfonic group | 91.4 | 92.5 | 99.6 |
| DIAION® SP85O | Styrene-divinylbenzene copolymer | None | 22.6 | 37.5 | No Crystallization |
| MACRONET® MN202 | Styrene-divinylbenzene copolymer | None | 25.4 | 44.5 | No Crystallization |
| AMBERLITE® XA1600 | Styrene-divinylbenzene copolymer | None | 25.8 | 31.8 | No Crystallization |
| DIAION® HP2MGL | Methacrylate polymer | None | 16.2 | 39.1 | No Crystallization |
| DIAION® WK10 | Methacrylate-divinylbenzene copolymer | Carboxyl group | 15.4 | 32.7 | No Crystallization |
| TRILITE® AMP16 | Styrene-divinylbenzene copolymer | Trimethylamine group | 13.5 | 38.9 | No Crystallization |
| TRILITE® AW90 | Styrene-divinylbenzene copolymer | Tertiaryamine group | 14.2 | 32.2 | No Crystallization |

When the styrene-divinylbenzene copolymer resin having a sulfonic group as a functional group was used as a stationary phase, all of the experimental results showed that the yield of the SMB chromatography process was more than 90%, that the content of L-cysteine was 92.5% or more, and that the purity of the L-cysteine hydrochloride monohydrate crystals was 99.5% or more. In contrast, when the crystals were obtained by employing the resins having a weakly acidic carboxyl group, a strong basic trimethylamine group, a weak basic tertiary amine group, or no functional group, the yield of the SMB chromatography process was 13.5% to 25.8% and the content of L-cysteine was 31.8% to 44.5%. That is, the yield and content were reduced by 50% or more compared to the yield and content obtained when a strongly acidic functional group was used as a stationary phase.

Based on this, it was confirmed that in the case where the resin having a strongly acidic functional group was used as a stationary phase when the fermentation broth of L-cysteine was separated and crystallized by the continuous chromatography, L-cysteine hydrochloride monohydrate crystals could be obtained with a high yield, concentration, and purity.

Experimental Example 2—Evaluation of Fermentation Broth Containing L-Cysteine According to pH In the Preparation Example (TRILITE® MCK32L used), L-cysteine hydrochloride hydrate crystals were prepared by only varying the pH of the fermentation broth containing L-cysteine. Specifically, after obtaining the fermentation broth containing L-cysteine in the same manner as in the Preparation Example, the pH of the fermentation broth was varied from 2.5 to 9.5 using 98% sulfuric acid or a 50% caustic soda solution.

Accordingly, the yield of the SMB chromatography process, the solid content of L-cysteine (%) in the separated liquid obtained through the SMB chromatography process, and the purity of the L-cysteine hydrochloride monohydrate crystals finally recovered were measured. The recovery rate of the SMB chromatography process was calculated as the recovery rate of L-cysteine in the separated liquid compared to the fermentation broth introduced into the SMB chromatography apparatus. The results are shown in Table 2.

TABLE 2

| pH of fermentation broth | Recovery rate of SMB chromatography (%) | Content of L-cystiene (%) | Purity of L-cysteine hydrochloride monohydrate crystals (%) |
|---|---|---|---|
| 2.5 | 30.1 | 81.3 | 98.2 |
| 3.0 | 59.4 | 85.4 | 98.9 |
| 3.5 | 68.2 | 90.1 | 99.6 |
| 4.0 | 76.5 | 91.2 | 99.5 |
| 4.5 | 88.2 | 93.7 | 99.6 |
| 5.0 | 90.2 | 94.5 | 99.7 |
| 5.5 | 92.4 | 93.2 | 99.7 |
| 6.0 | 91.8 | 92.1 | 99.5 |
| 6.5 | 89.4 | 92.7 | 99.4 |
| 7.0 | 86.1 | 92.2 | 99.5 |
| 7.5 | 69.2 | 90.3 | 99.3 |
| 8.0 | 60.3 | 88.4 | 99.0 |
| 8.5 | 58.2 | 87.9 | 99.1 |
| 9.0 | 50.4 | 85.7 | 98.7 |
| 9.5 | 22.7 | 58.2 | 75.6 |

The yield of the SMB chromatography process was found to be 50% or more at a pH range of 3.0 to 9.0, 85% or more at a pH range of 4.5 to 7.0, and 90% at a pH range of 5.0 to 6.0. The solid content of L-cysteine excluding moisture in the separated liquid obtained through the SMB chromatography process was 85% or more at a pH range of 3.0 to 9.0 and 90% or more at a pH range of 3.5 to 7.5.

In addition, the purity of the L-cysteine hydrochloride monohydrate crystals was found to be 98% or more at a pH range of 2.5 to 9.0 and 99% or more at a pH range of 3.5 to 8.5. That is, it was confirmed that when the method of the present disclosure was employed, the L-cysteine hydrochloride monohydrate crystals could be obtained with a very high purity without greatly affecting the pH range.

Experimental Example 3—Evaluation According to the Amount of Hydrochloric Acid Added In the Preparation Example (TRILITE® MCK32L used), L-cysteine hydrochloride hydrate crystals were prepared by only varying the [HCl]/[L-cysteine] equivalence ratio of hydrochloric acid added in the range of 0.80, 0.85, 0.90, 1.0, 1.5, 2.0, 2.5, 3.0, and 3.5.

Accordingly, the yield of the SMB chromatography and the purity of the L-cysteine hydrochloride monohydrate crystals finally recovered were measured. The recovery rate of the crystallization process was calculated as the recovery rate of L-cysteine contained in the L-cysteine hydrochloride monohydrate crystals finally recovered relative to L-cysteine in the separated liquid according to the SMB chromatography process. The results are shown in Table 3.

TABLE 3

| [HCl]/[L-cysteine] equivalence ratio | Type of crystals | Purity of L-cysteine hydrochloride monohydrate crystals (%) | Recovery rate of crystallization process (%) |
|---|---|---|---|
| 0.80 | L-Cysteine | — | — |
| 0.85 | L-Cysteine | — | — |
| 0.90 | L-Cysteine hydrochloride monohydrate | 99.5 | 43.7 |
| 1.0 | L-Cysteine hydrochloride monohydrate | 99.7 | 46.1 |
| 1.5 | L-Cysteine hydrochloride monohydrate | 99.5 | 60.2 |
| 2.0 | L-Cysteine hydrochloride monohydrate | 99.7 | 79.1 |
| 2.5 | L-Cysteine hydrochloride monohydrate | 99.6 | 64.9 |
| 3.0 | L-Cysteine hydrochloride monohydrate | 99.6 | 44.9 |
| 3.5 | L-Cysteine hydrochloride monohydrate | 99.7 | 24.8 |

All crystals were precipitated during the concentration, but when the [HCl]/[L-cysteine] equivalence ratio was 0.85 or less, the L-cysteine crystals were precipitated, and when the equivalence ratio was 0.9 or more, the L-cysteine hydrochloride monohydrate crystals were precipitated. That is, it can be interpreted that when the equivalence ratio was greater than 0.85, the L-cysteine hydrochloride monohydrate crystals were precipitated.

The purity of L-cysteine hydrochloride monohydrate crystals was found to be 98% or more when the L-cysteine hydrochloride monohydrate was formed regardless of the [HCl]/[L-cysteine] equivalence ratio. The recovery rate of the crystallization process for the L-cysteine hydrochloride monohydrate was found to be 40% or more at the [HCl]/[L-cysteine] equivalence ratio of 0.9 to 3.0, and it is expected to be more than 50% at the equivalence ratio greater than 1.0 and less than 3.0. In addition, the purity was found to be 60% or more at the equivalence ratio of 1.5 to 2.5, and it is predicted that there may be an optimum condition for reaching the highest recovery rate at the equivalence ratio of 1.5 to 2.5.

Experimental Example 4—Evaluation According to Concentration of Concentrate

In the Preparation Example (TRILITE® MCK32L used), L-cysteine hydrochloride hydrate crystals were prepared by only varying the concentration of the concentrate obtained by concentrating the separated liquid to which hydrochloric acid was added from 100 g/L to 900 g/L.

Accordingly, the time at which nucleation occurred, the purity of the L-cysteine hydrochloride monohydrate crystals finally recovered, and the recovery rate of the crystallization process were measured. The recovery rate of the crystallization process was calculated as the recovery rate of L-cysteine contained in the L-cysteine hydrochloride monohydrate crystals finally recovered relative to L-cysteine in the separated liquid according to the SMB chromatography process. The results are shown in Table 4.

TABLE 4

| Concentration (g/L) | Time at which nucleation occurred | Purity of L-cysteine hydrochloride monohydrate crystals (%) | Recovery rate of crystallization process (%) |
|---|---|---|---|
| 100 | No crystal formation | No crystal formation | 0 |
| 200 | During cooling | 99.8 | 28.3 |
| 300 | During concentration | 99.7 | 50.7 |
| 400 | During concentration | 99.5 | 62.1 |
| 500 | During concentration | 99.7 | 70.6 |
| 600 | During concentration | 99.6 | 73.4 |
| 700 | During concentration | 99.7 | 79.1 |
| 800 | During concentration | 99.1 | 83.2 |
| 900 | During concentration | No crystal separation due to solidification | No crystal separation due to solidification |

The nucleation of the L-cysteine hydrochloride monohydrate occurred when the concentration was 200 g/L or more, but the nucleation occurred during concentration when the concentration was 300 g/L or more, and it was possible to carry out rapid crystallization.

The purity of the L-cysteine hydrochloride monohydrate crystals was 99% or more in all cases where crystals were formed. That is, it was confirmed that when the crystals were obtained using the method of the present disclosure, the L-cysteine hydrochloride monohydrate crystals could be obtained with a very high purity regardless of the concentration of the separated liquid. The recovery rate of the crystallization process increased in proportion to the concentration. However, when the concentration was 800 g/L, L-cysteine crystals could be obtained with a high purity and a high recovery rate, whereas, when the concentration was 900 g/L, solidification of the L-cysteine hydrochloride monohydrate crystal slurry occurred, and accordingly, stirring and separation of the crystals were impossible. Thus, it is expected that L-cysteine crystals can be obtained with a high purity and a high recovery rate at a concentration less than 900 g/L.

Based on these results, it was confirmed that when the concentration of the separated liquid for the SMB chromatography was from 200 g/L to less than 900 g/L, the L-cysteine crystals were easily obtained. In particular, it was confirmed that when the concentration was in the range of 300 g/L to 800 g/L, the crystals could be obtained with a faster crystallization process, at a high purity and a high recovery rate.

Experimental Example 5—Evaluation According to Change of Cooling Condition at Low Concentration The concentrate, from which no L-cysteine hydrochloride monohydrate crystals were formed even when cooled to 15° C., when the concentration of the separated liquid for the SMB chromatography was 100 g/L in Example 4, was cooled to −10° C. at a constant cooling rate for 2 hours and 30 minutes in a jacket tank together with stirring, and then stirred at the same temperature as the temperature at the completion of cooling for 12 hours. As a result, L-cysteine hydrochloride monohydrate crystals were formed. The crystals were subjected to a solid-liquid separation using a reduced-pressure membrane filtration apparatus, added with 100 mL of a washing liquid, and dried in an oven dryer at 35° C. for 12 hours to reduce the residual moisture to 12.0% or less. Finally, L-cysteine hydrochloride monohydrate crystals were prepared. The purity of the L-cysteine hydrochloride monohydrate crystals was 99.8%, and the recovery rate of the crystallization process was found to be 9.7%.

Based on this, it was confirmed that even when the concentration of the separated liquid for the SMB chromatography was less than 200 g/L, the L-cysteine hydrochloride monohydrate crystals could be obtained by controlling the cooling temperature. However, the recovery rate of the crystallization process was too low to be applied industrially. In addition, there were disadvantages in that the cooling crystallization process must be carried out even under a harsh temperature condition below zero and that the crystallization time is long.

Experimental Example 6—Evaluation According to Cooling Temperature

In the Preparation Example, L-cysteine hydrochloride monohydrate crystals were prepared by only varying the cooling temperature of the L-cysteine hydrochloride monohydrate crystal slurry. Specifically, a total of 5 crystallization experiments were carried out including stirring the L-cysteine hydrochloride monohydrate crystal slurry at 55° C. for 2 hours without cooling, and cooling the L-cysteine hydrochloride monohydrate crystal slurry to a various temperature range from 0° C. to 45° C. with a cooling rate of 10° C./h while stirring. The initial volume of the L-cysteine hydrochloride monohydrate slurry used in each experiment was 1 L.

Accordingly, the purity of the L-cysteine hydrochloride monohydrate crystals and the recovery rate of the crystallization process are shown in Table 5. The recovery rate of the crystallization process was calculated as the recovery rate of L-cysteine contained in the L-cysteine hydrochloride monohydrate crystals finally recovered relative to the L-cysteine in the separated liquid according to the SMB chromatography process. The results are shown in Table 5.

TABLE 5

| Cooling temperature (° C.) | Purity of L-cysteine hydrochloride monohydrate crystals (%) | Recovery rate of crystallization process (%) |
| --- | --- | --- |
| 0 | 99.5 | 83.5 |
| 15 | 99.7 | 79.1 |
| 30 | 99.7 | 74.2 |
| 45 | 99.8 | 68.9 |
| 55 (No crystallization) | 99.8 | 64.3 |

The purity of the L-cysteine hydrochloride monohydrate crystals was 99.5% or more in all cases. In addition, the recovery rate of the crystallization process was 64% or more even when cooling did not occur, and the recovery rate of the crystallization process increased as the cooling temperature decreased. The process recovery rate was found to be 70% or more at a temperature below 45° C., and it was expected that the process recovery rate would be 74% or more at a temperature 30° C. or below.

Example 7—Evaluation According to Concentration of Fermentation Broth Containing L-Cysteine Used as Source Material for SMB Chromatography In the Preparation Example, L-cysteine hydrochloride hydrate crystals were prepared by only varying the concentration of the fermentation broth (pH 5.5) containing L-cysteine used as a source material for SMB chromatography. Specifically, a total of 6 experiments were conducted including using the L-cysteine fermentation broth having a concentration of 26 g/L obtained in the Preparation Example as a source liquid for SMB chromatography, using a fermentation broth having an L-cysteine concentration of 10 g/L as a source liquid for SMB chromatography by dilution with water, and using a fermentation broth having an L-cysteine concentration from 60 g/L to 150 g/L as a source liquid for SMB chromatography by concentration using a thin-film evaporator. When the concentration of L-cysteine was increased to 180 g/L, the SMB chromatography process was not carried out as the L-cysteine crystals were precipitated.

The volume of the source liquid used in each experiment was 0.1 kL or more. The yield of the SMB chromatography process and the solid content of L-cysteine excluding moisture in the process liquid produced by SMB chromatography are shown in Table 6.

TABLE 6

| Concentration of L-cysteine in source liquid for SMB chromatography (g/L) | Yield of SMB chromatography process (%) | Solid content of L-cysteine in separated liquid (%) |
| --- | --- | --- |
| 10 | 90.3 | 94.2 |
| 26 | 91.5 | 93.0 |
| 60 | 90.9 | 93.4 |
| 90 | 91.8 | 92.8 |
| 120 | 92.4 | 93.2 |
| 150 | 92.0 | 93.2 |

The yield of the SMB chromatography process was 90% or more in all sections, and the solid content of L-cysteine excluding moisture in the process liquid produced by SMB chromatography was 90% or more in all sections. According to the above results, it can be interpreted that the method for purifying L-cysteine by SMB chromatography of the present disclosure is very effective for purifying and crystallizing the fermentation broth containing L-cysteine regardless of the concentration of L-cysteine in the source liquid.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for preparing L-cysteine hydrochloride hydrate crystals, comprising:
   (a) obtaining a separated liquid after introducing a fermentation broth in a pH range of 3.0 to 9.0 containing L-cysteine into a continuous chromatography apparatus having a strongly acidic cation exchange resin as a stationary phase, wherein the strongly acidic cation exchange resin comprises a sulfonic acid functional group, and the continuous chromatography excludes adsorption or elution of L-cysteine;
   (b) adding hydrochloric acid to the separated liquid such that an equivalence ratio ([HCl]/[L-cysteine]) of hydrochloric acid to L-cysteine is from 0.9 to 3.0;
   (c) concentrating the separated liquid to which hydrochloric acid is added to form a concentrate; and
   (d) recovering L-cysteine hydrochloride hydrate crystals from the concentrate.

2. The method of claim 1, further comprising adjusting the fermentation broth containing L-cysteine to a pH of 3.5 to 7.5 prior to step (a).

3. The method of claim 1, further comprising concentrating the fermentation broth in a pH range of 3.0 to 9.0 containing L-cysteine prior to step (a).

4. The method of claim 1, wherein the strongly acidic cation exchange resin is a styrene-divinylbenzene copolymer.

5. The method of claim 1, wherein the continuous chromatography apparatus is a simulated moving bed (SMB) chromatography apparatus.

6. The method of claim 1, wherein the separated liquid in step (a) has a solid content of L-cysteine excluding moisture of 85% (w/w) or more.

7. The method of claim 1, wherein a recovery rate of the continuous chromatography process, as a ratio of L-cysteine in the separated liquid obtained relative to the fermentation broth introduced, is 50% (w/w).

8. The method of claim 1, wherein the equivalence ratio ([HCl]/[L-cysteine]) of hydrochloric acid to L-cysteine in step (b) is from 1.5 to 2.5.

9. The method of claim 1, wherein step (c) is carried out such that a concentration of L-cysteine in the separated liquid, to which hydrochloric acid is added, is from 200 g/L to less than 900 g/L.

10. The method of claim 1, wherein step (c) is carried out such that a concentration of L-cysteine in the separated liquid, to which hydrochloric acid is added, is from 500 g/L to less than 900 g/L.

11. The method of claim 1, further comprising cooling the concentrate prior to step (d).

12. The method of claim 11, wherein the concentrate is cooled to a temperature from 0° C. to 30° C.

13. The method of claim 1, further comprising adding a filtrate obtained by recovering the crystals in step (d) to the fermentation broth, the separated liquid of step (b), or the separated liquid to which hydrochloric acid is added.

14. The method of claim 1, wherein a purity of the prepared L-cysteine hydrochloride hydrate crystals is 98% (w/w) or more.

* * * * *